United States Patent [19]

Junius-Comer et al.

[11] Patent Number: 5,654,163
[45] Date of Patent: Aug. 5, 1997

[54] INDOPHENOL SUBSTITUTED MALTOOLIGOSIDES AS α-AMYLASE SUBSTRATES

[75] Inventors: Martina Junius-Comer, Iffeldorf; Axel Schmidt; Elli Rauscher, both of München, all of Germany

[73] Assignee: Boehringer Mannheim GmbH, Mannheim-Waldhof, Germany

[21] Appl. No.: 506,261

[22] Filed: Jul. 24, 1995

Related U.S. Application Data

[63] Continuation of Ser. No. 962,200, filed as PCT/EP92/00888, Apr. 22, 1992, abandoned.

[30] Foreign Application Priority Data

Apr. 23, 1991 [DE] Germany .................. 41 13 238.6

[51] Int. Cl.$^6$ .................. C12Q 1/40; C12Q 1/54; C12N 9/26; C07H 1/00
[52] U.S. Cl. .................. 435/22; 435/14; 435/4; 435/183; 435/201; 536/1.11; 536/4.1
[58] Field of Search .................. 435/22, 14, 4, 435/201, 183; 536/1.11, 4.1

[56] References Cited

U.S. PATENT DOCUMENTS

| | | | |
|---|---|---|---|
| 4,622,295 | 11/1986 | Ikenaka et al. | 435/22 |
| 4,697,006 | 9/1987 | Ikenaka et al. | 536/17.2 |
| 4,762,917 | 8/1988 | Ikenaka et al. | 536/4.1 |
| 4,863,728 | 9/1989 | Gerber et al. | 435/201 |
| 4,963,479 | 10/1990 | Chavez et al. | 435/22 |

FOREIGN PATENT DOCUMENTS

| | | |
|---|---|---|
| 510620A1 | 10/1992 | European Pat. Off. . |
| 2306991 | 12/1990 | Japan . |
| 02306990 | 12/1990 | Japan . |

OTHER PUBLICATIONS

Takeo, Kenichi; Chem Abstract 86(9):55645v (1976).

Primary Examiner—Gary L. Kunz
Assistant Examiner—Louise Leary
Attorney, Agent, or Firm—Felfe & Lynch

[57] ABSTRACT

The invention concerns new indophenyl-substituted maltose derivatives, their use for the determination of the enzymatic activity of α-amylase and reagents for the determination of α-amylase which contain the new indophenyl-substituted maltose derivatives as the enzyme substrate.

21 Claims, 1 Drawing Sheet

2',2,6-TRICHLOROINDOPHENYL-ALPHA - MALTOTRIOSIDE:

2,6-DICHLOROINDOPHENYL-ALPHA - MALTOTRIOSIDE:

2,6-DIMETHYLINDOPHENYL-ALPHA - MALTOTRIOSIDE:

2',2,6-TRICHLOROINDOPHENYL-
ALPHA - MALTOTRIOSIDE:

Fig. 1

2,6-DICHLOROINDOPHENYL-
ALPHA - MALTOTRIOSIDE:

2,6-DIMETHYLINDOPHENYL-
ALPHA - MALTOTRIOSIDE:

INDOPHENOL SUBSTITUTED MALTOOLIGOSIDES AS α-AMYLASE SUBSTRATES

This application is a continuation of application Ser. No. 07/962,200, filed as PCT/EP92/00888, Apr. 22, 1992, now abandoned.

DESCRIPTION

The invention concerns maltosides and maltotriosides, the reducing ends of which are linked to a substituted indophenol residue in the α-configuration and concerns the use of these compounds as synthetic enzyme substrates for the direct determination of α-amylase, in particular for the determination of pancreas α-amylase as well as a suitable reagent therefore.

α-Amylase (E.C. 3.2.1.1) degrades 1,4-α-glucosidically-linked oligosaccharides and polysaccharides, mainly by hydrolysis of the 1,4-α-glucosidic bonds, to maltose and maltooligosides. Apart from the use in industrial fermentation techniques, the enzyme has considerable importance in the field of clinical analysis and diagnostics. In particular, the determination of pancreas α-amylase is of considerable diagnostic importance since the amount of this enzyme in body fluids such as serum, urine or duodenal secretions changes substantially in numerous diseases.

Numerous methods and synthetic enzyme substrates are known for the determination of α-amylase.

EP-A 0346 912 discloses maltooligosides whose reducing ends are linked to a phenyl residue in the α- or β-configuration which is substituted in the para position by a nitro or a nitrovinyl group. These maltooligosides are described as being suitable substrates for the determination of the activity of hydrolases, lipases, esterases, α-glucosidases or glucoamylases.

EP-A 0 319 933 discloses maltooligosides whose non-reducing ends are not blocked by protecting groups and whose reducing ends are linked with substituted or non-substituted phenyl residues in the α- or β-configuration. Examples of substituted phenyl residues are halogen-, hydroxyl-, alkyl-, alkoxy-, alkoxycarbonyl-, nitro- and phenol-substituted phenyl residues. The phenyl residue is most preferably substituted by one or several nitro groups. β-linked maltooligosides of the above type are described as being suitable for the determination of α-amylase in the presence of auxiliary enzymes such as α-glucosidase and β-glucosidase. A direct determination of α-amylase in the absence of auxiliary enzymes is not disclosed.

The Japanese specification 64-42497 discloses maltooligosides which are substituted at their reducing ends with an indophenol residue in the β-configuration having the formula in which $X_1$ to $X_6$ denote hydrogen atoms or halogen atoms or nitro, cyano, azide, acyl, sulfonic acid, nitroso, sulfonyl, sulfoxyl, thiocyano, isothiocyano, isonitrile, imino, azo, diazo, alkyl, allyl, or aryl groups where $X^3$ and $X^4$ and/or $X^5$ and $X^6$ can be linked and can form condensed aromatic rings.

In addition processes for the production of these compounds are disclosed as well as their use as α-amylase substrates in the presence of α- and β-glucosidase. There is a concrete disclosure in the examples of the production of the compounds phenolindo-3'-chlorophenyl-β-maltopentaoside, hexadecaacetyl-(phenolindo-3',5'-dichlorophenyl)-β-maltopentaoside, phenolindo-3',5'-dichlorophenyl-β-maltoheptaoside, hexadecaacetyl-(2,5-dimethylphenolindo-3'-chlorophenyl-β)-pentaoside and hexadecaacetyl-(1-naphtholindo-3'-chlorophenyl)-β-pentaoside.

EP-A 0 263 435 discloses aromatically substituted glycosides having the formula in which the substituent R at the reducing end of the compound is in the α-configuration, n=0 or 1 and R is a substituted aromatic residue selected from the group in which $R_1$ through $R_6$ independent of one another halogen, $NO_2$, $SO_3H$, where $R^7$ is lower alkyl residue including its stereoisomers, optical isomers and geometric isomers and mixtures of these isomers. These substrates are described as being direct substrates (i.e. without the presence of auxiliary enzymes) for α-amylases. The examples specifically disclose the production of 2-chloro-4-nitrophenyl-α-D-maltotrioside, 4-chloro-2-nitro-1-naphthyl-α-maltotrioside and 2-formyl-4-nitrophenyl-α-D-maltotrioside. In addition a process for the production of the substrates and related substances is disclosed. The compounds disclosed in EP-A 0 263 435 have a maximum absorbance at wavelengths of ca. 385 to 450 nm.

The Japanese specification 02/306990 describes indophenyl-α-glycosides with 2 to 10 glucose units, indophenyl residues as the chromophores and unsubstituted OH groups on the oligoglucoside. The disclosed example is phenolindo-3'-chlorophenyl-α-D-maltopentaoside the determination of which is carried out in the presence of the auxiliary enzyme α-glucosidase.

The Japanese specification 02/306991 discloses cyclic acetals of indophenyl-glucosides with an α- or β-linkage and 2 to 10 glucose units, which have indophenol residues as the chromophore and in which the OH groups at positions $C_4$ and $C_6$ of the glucose at the non-reducing end are substituted by alkyl or alkylidene residues. Compounds with 5 to 7 glucose units are referred to as being preferred. The disclosed example is isopropylidene-phenolindophenyl-α-maltopentaoside the determination of which is carried out in the presence of the auxiliary enzymes α-glucosidase and β-glucosidase.

The Japanese specification 03/085996 discloses indophenyl-β-maltooligosides with 3 to 8 glucose units which have indophenyl residues as the chromophore and unsubstituted or acyl-substituted OH groups and in which the OH groups at positions $C_4$ and $C_6$ of the glucose at the non-reducing end are substituted if desired with alkylidene groups. Isopropylidene-phenolindophenyl-β-D-maltopentaoside is disclosed as an example the determination of which is carried out in the presence of the auxiliary enzymes α-glucosidase and β-glucosidase.

However, all the above-mentioned methods and enzyme substrates for the determination of α-amylase have disadvantages. Thus the above-mentioned compounds with 5 or more glucose units in which the substituent at the reducing end of the sugar is linked in the α- or β-configuration are only suitable for the determination of α-amylase in the presence of auxiliary enzymes and not as direct substrates. Other substances are unsuitable as substrates because they have a low sensitivity and their absorbance maxima are at unfavourable wavelengths. Thus it is known for example that when α-amylase tests are carried out at wavelengths below 500 nm, interferences can occur which are due to compounds present in body fluids such as haemoglobin and bilirubin.

One object of the present invention is therefore to provide α-amylase substrates which absorb in the long wavelength region i.e. above ca. 550 nm and which can be cleaved directly by α-amylase without the necessity for auxiliary enzymes.

The object according to the present invention is achieved by compounds having the general formula I in which Gluc is a glucose molecule and the indophenyl residue is linked to the sugar in the α-configuration, n=1 or 2, $R^1$=H, a straight-chained or branched alkyl or alkoyl group with 1 to 6 C atoms, a cycloalkyl or cycloalkoyl group with 3 to 6 C atoms, a benzoyl, benzyl or phenyl group, $R^2$=H, or in which $R^1$ and $R^2$ together form a methylene bridge, each of the H atoms of which can be independently substituted by an alkyl group with 1 to 5 C atoms or a phenyl group, $R^3$, $R^4$, $R^5$, $R^6$ are independently of one another H, a halogen (F, Cl, Br), nitro, acetamide or cyano group, a sulfonic acid group, sulfinic acid group or carboxylic acid group as well as the corresponding acid alkyl ester groups and acid amide groups, an alkoxy group, a straight-chained or branched alkyl group with 1 to 6 C atoms which is substituted if desired, a cycloalkyl group with 3 to 6 C atoms which is substituted if desired or an aryl group which is substituted if desired, whereby $R^3$ and $R^4$ or/and $R^5$ and $R^6$ can be linked to one another and can form condensed rings, X, Y are independently of one another H, a halogen (F, Cl, Br), nitro, acetamide or cyano group, a sulfonic acid group, sulfinic acid group or carboxylic acid group as well as the corresponding acid alkyl ester groups and acid amide groups, an alkoxy group, a straight-chained or branched alkyl group with 1 to 6 C atoms which is substituted if desired, a cycloalkyl group with 3 to 6 C atoms which is substituted if desired or an aryl group which is substituted if desired, provided that X and Y are not simultaneously H.

The said aryl group in the above definitions is preferably phenyl or naphthyl. The alkoxy group can contain one or several 0 bridges, it can therefore for example also be a polyethylene glycol chain. The alkyl, cycloalkyl and aryl residues are substituted if desired, i.e. they can carry substituents (such as e.g. halogen groups) which do not react with α-amylase under the conditions prevailing in the enzymatic determination test.

The compounds of the general formula I are surprisingly very well suited as synthetic enzyme substrates for α-amylase since they can be cleaved directly (i.e. in the absence of auxiliary enzymes) by α-amylase and at the same time absorb in the long wavelength range above ca. 550 nm. The ability to use substances according to the present invention is even more surprising since compounds with an analogous structure in which hydrogen atoms are present at both positions X and Y of the phenyl ring in the indophenol residue cannot be directly cleaved by α-amylase.

The substituents $R^1$ and $R^2$ at the non-reducing end of compound I are preferably hydrogen atoms. However, it is also possible to block compound I at these positions by substituents. The introduction of such substituents is described in detail in DE-39 29 355. Accordingly residues $R^1$ and $R^2$ can be introduced starting from the corresponding unsubstituted compounds I by reacting these with a dialkoxy compound under etherification conditions, preferably with dialkoxyethane or the corresponding benzyl derivative, to form a compound of the general formula I in which $R^1$ and $R^2$ together form a methylene group which is substituted if desired.

The desired substituent group can also be introduced into the unprotected substrate via activated carboxylic acid groups such as e.g. via the corresponding orthoesters, acid chlorides, anhydrides or enzymatically from activated esters (J.A.C.S 110 (1988), 584–589) or from acetals or directly from the carboxylic acid via dehydrating agents such as e.g. by the Mitsunobu reaction (Tetrahedron Letters Vol. 30 (1989), 325–326). Particularly preferred is the production which proceeds via the corresponding orthoesters as intermediate products and production by means of the Mitsunobu reaction. The orthoesters are preferably prepared from the corresponding nitriles (cf. e.g. Houben-Weyl, Vol. VI/3 (1965), 300–313). The purification of these protected substrates can for example be carried out chromatographically by means of ion exchangers or HPLC.

In the general formula I, n=1 or 2, and thus the compounds according to the present invention are maltosides or maltotriosides. Higher maltooligosides are no longer accepted by the α-amylase as direct substrates. The compounds according to the present invention are preferably maltotriosides.

The residues X and Y on the phenyl ring of the indophenol residue of I can be independently of one another H, a F, Cl, or Br, acetamide, nitro or cyano group, a sulfonic acid, sulfinic acid or carboxylic acid group as well as corresponding acid alkyl ester and acid amide groups, an alkoxy group (with one or several oxygen bridges, i.e. for example also a polyethylene glycol chain), a straight-chained or branched alkyl group with 1 to 6 C atoms which is substituted if desired, a cycloalkyl group with 3 to 6 C atoms which is substituted if desired or an aryl group which is substituted if desired provided that X and Y are not simultaneously H. Those of the compounds of formula I in which one or both of the residues X and Y are hydrogen and the other residue represents a substituent which is different from hydrogen are in general preferred. It is also preferred that at least one of X and Y is a halogen group, it is particularly preferred that X is a halogen group and Y is hydrogen. It is most preferred when the halogen group denotes chlorine.

The residues $R^3$, $R^4$, $R^5$ and $R^6$ in the general formula I represent the possible substituents on the benzoquinone ring of the indophenol residue. In this case $R^3$, $R^4$, $R^5$ and $R^6$ can be independently of one another H, a halogen (F, Cl, Br), nitro, acetamide or cyano group, a sulfonic acid group, sulfinic acid group or carboxylic acid group as well as the corresponding acid alkyl ester and the acid amide groups, an alkoxy group, a straight-chained or branched alkyl group with 1 to 6 C atoms which is substituted if desired, a cycloalkyl group with 3 to 6 C atoms which is substituted if desired or an aryl group which is substituted if desired, whereby $R^3$ and $R^4$ or/and $R^5$ and $R^6$ can be linked together and can form condensed rings whereby the alkoxy group can have one or several 0 bridges. If the residues $R^3$ and $R^4$ or/and the residues $R^5$ and $R^6$ are linked together, condensed rings are formed. The resulting compounds I with such a substitution pattern are also suitable as direct α-amylase substrates.

$R^3$ and $R^5$ preferably denote hydrogen and $R^4$ and $R^6$ preferably denote halogen, particularly preferably chlorine. Of the compounds having the general formula I 2',2,6-trichloro-indophenyl-α-maltotrioside is most preferred which as a result of its long wavelength absorbance can be determined at a measurement wavelength of 645 nm and can be cleaved excellently by α-amylase in the absence of auxiliary enzymes.

The compounds according to the present invention are produced in a known manner whereby three different processes can be described as being preferred. In the first and preferred process variant one starts with maltose or maltotriose. These compounds are peracetylated in a known way under sodium acetate catalysis (e.g. by reaction with acetic acid anhydride) whereby a compound having the general formula II is produced in which Ac-Gluc denotes a peracetylated glucose and the acetyl residue at the reducing end of II is linked in the β-configuration to the sugar.

The compound II is subsequently reacted in the presence of an acid catalyst with a substituted p-nitrophenol having the general formula III in which X and Y have the meanings stated above. Suitable acid catalysts for this reaction are e.g. alkylsulfonic or arylsulfonic acids such as p-toluenesulfonic acid or preferably Lewis-acid catalysts such as $BF_3.OEt_2$. This reaction is a stereospecific substitution of the acetyl residue at the reducing end of the sugar by the p-nitrophenol III which in formal terms proceeds according to a $S_N2$ mechanism so that the p-nitrophenyl residue is linked in an α-configuration to the sugar in the resulting compound IV.

Subsequently the nitro group of IV is reduced to an amino group in a known manner (e.g. by catalytic hydrogenation in the presence of Pd-C). Afterwards the acetyl residues are cleaved from the resulting compound e.g. by alkaline saponification in the presence of ammonia.

The deacetylated product is finally reacted with a p-benzoquinone, which is substituted if desired, of the general formula V in which $R^3$, $R^4$, $R^5$ and $R^6$ have the meanings stated above. In this way a compound having the general formula VI is produced in which the indophenol residue is linked to the sugar in the α-configuration. This reaction is preferably carried out in an anhydrous aprotic solvent such as dimethylformamide or dioxan or a mixture thereof in the presence of trifluoroacetic acid.

If desired, the hydrogen atoms at positions 4 and 6 of the glucose residue at the non-reducing end of the sugar can be substituted by the residues $R^1$ and $R^2$ in a further step as already elucidated in detail above.

Alternatively the production of the compound according to the general formula I can be carried out by reacting a peracetylated β-maltose or β-maltotriose with an indophenol having the general formula VII (VII)

in which X, Y, R³, R⁴, R⁵ and R⁶ have the meanings stated above. The further processing of the resulting product, i.e. deacetylation and, if desired, derivatization at the non-reducing end, is carried out in an analogous manner to the first process variant.

A third way of producing the compounds according to the present invention is to firstly synthesize an indophenol-α-glucoside derivative having the general formula VIII according to one of the aforementioned processes, (VIII)

in which the respective residues have the meanings stated above and this compound is subsequently converted into the maltoside or maltotrioside derivatives according to the present invention by "trimming" in the presence of cyclodextrin, amylose or starch in the presence of cyclodextrin-glucosyltransferase.

Processes for the production of β-maltooligoside derivatives which differ from the compounds according to the present invention in the configuration of the substituent at the reducing end of the sugar are disclosed in detail in the Japanese specification 64-42497 for the corresponding indophenyl-β-glucoside derivatives. The production of the α-maltooligoside derivatives according to the present invention in principle only differs in that one starts with a peracetylated β-maltooligoside derivative whereas the production of the β-compounds starts with a peracetylated α-maltooligoside derivative.

The production of α-maltooligoside derivatives which differ from the substances according to the present invention in the type of substituents is disclosed in EP-A 0 263 435.

The present invention also concerns a method for the determination of the activity of α-amylase in an aqueous solution, in particular in body fluids, with a synthetic enzyme substrate in which a compound of the general formula I as claimed in claim 1 is used as the enzyme substrate. In this method a compound I is preferably used in which R¹ and R² denote hydrogen or together form a methylene bridge whose hydrogen atoms can independently each be substituted by an alkyl group with 1 to 5 C atoms or by a phenyl group. In addition it is preferred that one of the substituents X and Y on the phenyl ring of the indophenyl residue is hydrogen and that the other substituent is different from hydrogen. Furthermore it is preferred that at least one of the residues X and Y denotes a halogen group. The use of 2',2,6-trichloro-indophenyl-α-maltotrioside as an enzyme substrate is particularly preferred.

The method according to the present invention enables a direct determination of the activity of α-amylase i.e. a determination of activity in the absence of auxiliary enzymes such as α-glucosidase or β-glucosidase.

Moreover it is possible to use the method according to the present invention to specifically determine the activity of pancreatic α-amylase in the presence of salivary α-amylase using a specific inhibitor system for salivary α-amylase. Such an inhibitor system which comprises one or several monoclonal antibodies is disclosed for example in DE 39 29 355. Suitable antibodies are for example disclosed in EP-A 0 191 284, in EP-A 0 150 309 and in EP-A 0 209 154. Pancreatic α-amylase can be determined very selectively and very accurately by combining the enzyme substrate according to the present invention and the inhibitor substance.

The present invention in addition concerns a reagent for the direct, specific determination of α-amylase with a synthetic enzyme substrate which contains a compound having the general formula I as the enzyme substrate. The reagent according to the present invention preferably contains a compound I as enzyme substrate in which R¹ and R² denote hydrogen or together form a methylene bridge, the hydrogen atoms of which can each be independently substituted by an alkyl group with 1 to 5 C atoms or by a phenyl group. In addition it is preferred that one of the substituents X and Y in the substrate used having the formula I is hydrogen and the other substituent is different from hydrogen. Furthermore it is preferred that at least one of the residues X and Y denotes a halogen group. A reagent according to the present invention containing 2',2,6-trichloro-indophenyl-α-maltotrioside as the substrate is particularly preferred. The final concentration of the substrate according to the present invention in the enzyme test solution is preferably 1 to 10 mmol/l, particularly preferably 3 to 7 mmol/l. The reagent according to the present invention can also additionally contain an activator for α-amylase e.g. an azide or thiocyanate salt. The activator is preferably used at a final concentration of 50 to 700 mmol/l, particularly preferably 100 to 500 mmol/l. In addition the reagent according to the present invention can also contain a specific inhibitor system for salivary α-amylase which comprises one or several monoclonal antibodies. In this way it is possible to carry out a selective determination of pancreatic α-amylase.

Furthermore the invention concerns the use of a compound having the general formula I as a synthetic enzyme substrate, in particular for the direct determination of the enzymatic activity of α-amylase.

The invention is elucidated further by the following examples in conjunction with the figure.

EXAMPLE 1

Synthesis of 2',2,6-trichloro-indophenyl-α-maltotrioside a) Deca-acetyl-(2-chloro-4-nitrophenyl)-α-maltotrioside 0.1 mol peracetylated β-maltotriose, 0.3 mol 2-chloro-4-nitrophenol and 25 ml $BF_3.OEt_2$ are stirred for 32 hours at 45° C. in a mixture of 450 ml anhydrous toluene and 100 ml anhydrous dichloroethane while excluding moisture. Subsequently 500 ml dichloromethane is added and it is shaken with 800 ml saturated $Na_2CO_3$ solution. The organic phase is concentrated after drying over $MgSO_4$. The residue is chromatographed over silica gel (mobile solvent: ethyl acetate/hexane 2:1).

Yield: 27 g (25%)

TLC: $R_f$=0.59 (silica gel; toluene/acetone 7/4)

b) Deca-acetyl-(2-chloro-4-aminophenyl)-α-maltotrioside 6.5 g (6 mmol) of the product from 1a) is dissolved in a mixture of 160 ml dioxan, 60 ml methanol, 2 ml glacial acetic acid and 0.65 g 10% Pd-C is added. The hydrogenation is carried out for 7 hours at a pressure of 0.9 bar. After removing the catalyst by filtration and removal of the solvent, the residue is purified by silica gel chromatography (mobile solvent: toluene/acetone 7:3).

Yield: 1.6 g (25%)

TLC: $R_f$=0.42 (silica gel; toluene/acetone 7/4)

c) 2-chloro-4-aminophenyl-α-maltotrioside 1 g (1 mmol/l) of the product from 1b) is added to 50 ml methanol, 5 ml water and 10 ml 25% ammonia and stirred for 20 hours at room temperature. The solvent is removed and the product is reacted further without further purification.

Yield: 680 mg

TLC: $R_f$=0.47 (silica gel; butanol/glacial acetic acid/water 10/3/5)

d) 2',2,6-trichloro-indophenyl-α-maltotrioside 680 mg of the product from 1c) are dissolved in 10 ml anhydrous dimethylformamide, 30 ml anhydrous dioxan, 0.2 ml trifluoroacetic acid and 1 g (5.8 mmol) 2,6-dichlorobenzoquinone and 3 spatula-tipfulls of a molecular sieve are added. The mixture is stirred for 2 hours at room temperature while excluding moisture. It is subsequently filtered, concentrated, and the residue is taken up in water and filtered again. The filtrate is pretreated by means of gel chromatography (LH 20, mobile solvent: water). It is finally purified by means of preparative HPLC (RP 18; gradient: water/isopropanol; 0.1% trifluoroacetic acid: 80/20%→65/35%).

Yield: 60 mg (8%)

TLC: $R_f$=0.62 (silica gel; butanol/glacial acetic acid/water 10/3/5)

EXAMPLE 2

Figure 1:
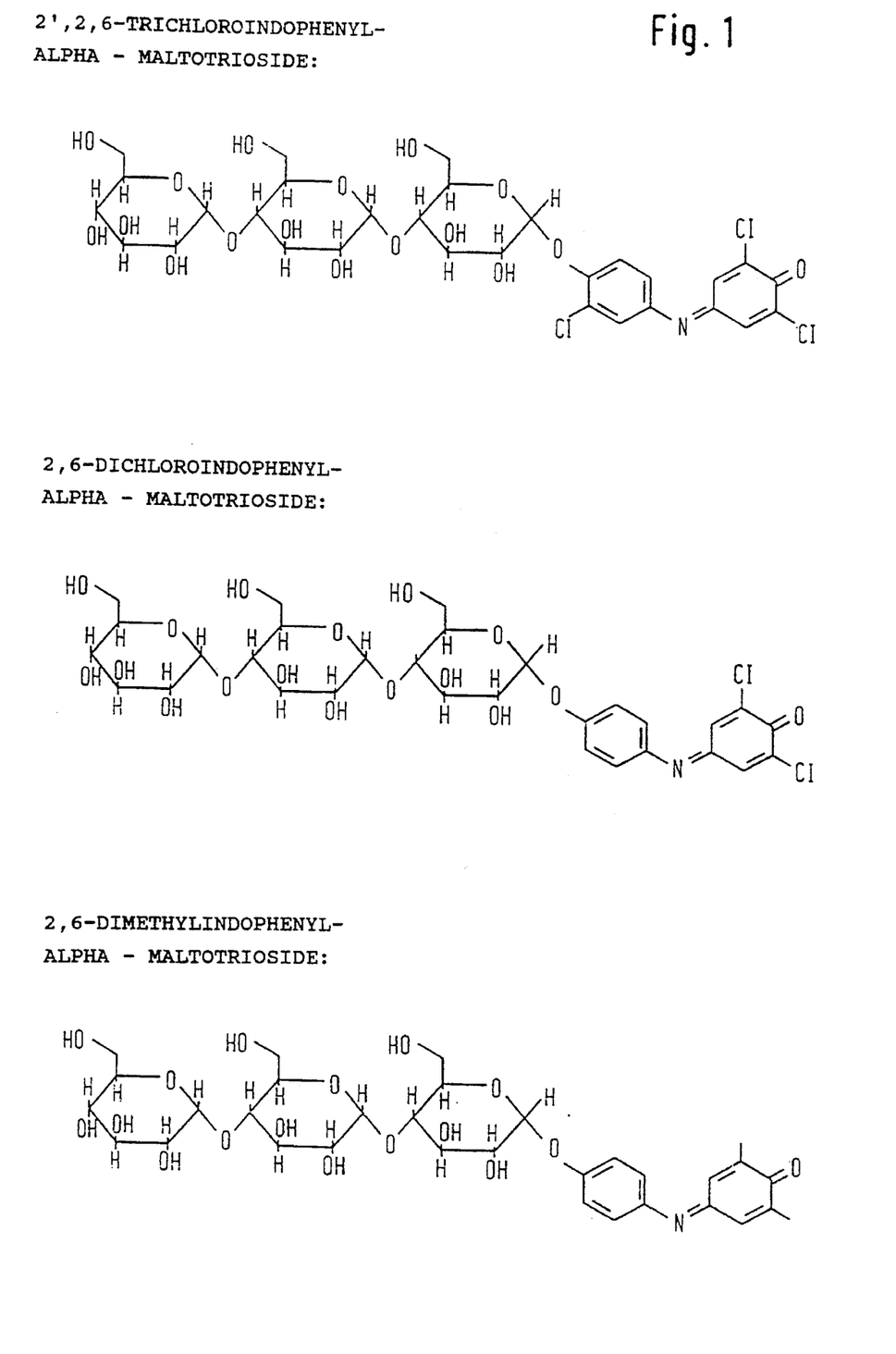
FIG. 1 shows the chemical structural formulae for the α-amylase substrates tested in example 2.

Use of 2',2,6-trichloro-indophenyl-α-maltotrioside as substrate for the direct determination of α-amylase The amylase activity of human pancreatic α-amylase (HPA) and human salivary α-amylase (HSA) was examined with the substrates listed in the following table and in FIG. 1. The following reagents were used:

| Reagent 1: | |
| --- | --- |
| 4-morpholino-ethane sulfonate (=MES) buffer | 61.6 mmol/l pH 6.0 |
| containing NaCl | 57.1 mmol/l |
| calcium acetate | 5.6 mmol/l |
| Reagent 2: | 49.3 mmol/l |
| Substrate (as stated in the table) | |

Reagent 1 also contains an activator, if desired, as stated in the table as well as antibodies produced by the cell lines NCACC 84122003 (MAB I) and NCACC 84111301 (MAB II) as inhibitors for salivary α-amylase. In order to carry out the determination 1.00 ml reagent 1 is mixed with 0.02 ml sample and pre-incubated at 37° C. Subsequently 0.10 ml reagent 2 is added, mixed and the absorbance at the respective measurement wavelength (see table) is read after one, two and three minutes. The mean of the absorbance difference/minute is calculated.

$$U/L \text{ sample} = \frac{\Delta A/\min \times 1.12 \times 1000}{\epsilon \times 0.02}$$

The final concentrations in the test mixture are:

| | |
| --- | --- |
| MES buffer, pH 6.0 | 55 mmol/l |
| NaCl | 51 mmol/l |
| calcium acetate | 5 mmol/l |
| substrate | 4.44 mmol/l |
| optionally activator | 152 mmol/l |
| sodium azide or potassium thiocyanate | 400 mmol/l |
| MAB I | ca. 5 to 8 mg/l |
| MAB II | ca. 2 to 3 mg/l |

Human pancreatic amylase (HPA) is used as the sample. The measurement is carried out at 37° C. at the measurement wavelength stated in each case. The results are shown in the table.

TABLE

| Substrate | Measurement wavelength [nm] | 400 mmol/l KSCN HPA [ΔA/min] |
| --- | --- | --- |
| 2',2,6-trichloro-indophenyl-α-maltotrioside | 645 | 0.063 |
| 2,6-dimethyl-indophenyl-α-maltotrioside | 578 | 0* |
| 2,6-dichloro-indophenyl-α-maltotrioside | 578 | 0 |

*With 150 mmol/l NaN$_3$ instead of KSCN

The results obtained show that only indophenyl derivatives which have a substituent which is different from hydrogen, in particular a halogen substituent, at position 2' of the phenyl ring constitute direct amylase substrates. If there is no substituent at the 2 position then there is no amylase cleavage.

EXAMPLE 3 a) Isopropylidene-2-chloro-4-nitrophenyl-α-D-maltotrioside 14.25 g deca-acetyl-(2-chloro-4-nitrophenyl)-α-maltotrioside from example 1a) is dissolved in 450 ml methanol. 45 ml water and 90 ml concentrated aqueous ammonia solution are added to this and it is stirred for 16 hours at room temperature. It is concentrated and 660 mg (1 mmol) of the 2-Cl-4-nitrophenyl-α-D-maltotrioside obtained is dissolved in 15 ml DMF. 1.25 ml (10 mmol) 2,2-dimethoxypropane (Merck 802936) and 172 mg (1 mmol) anhydrous p-toluene-sulfonic acid are added in succession. It is allowed to react for 80 minutes at 48° C. while stirring. The mixture is then added dropwise to 15 ml 0.24 mol/l NaHCO$_3$ solution. The mixture is shaken twice with 40 ml ethyl acetate in each case. The aqueous phase is concentrated and subsequently chromatographed on a Sephadex LH20 column (Pharmacia).

Eluent: water.

The suitable fractions are lyophilized.

Yield: 150 mg

TLC: $R_f$=0.51 (silica gel TLC, Merck 5735, mobile solvent 1-butanol/glacial acetic acid/water=10/3/5)

b) Isopropylidene-2-chloro-4-aminophenyl-α-D-maltotrioside 150 mg isopropylidene-2-chloro-4-nitrophenyl-α-D-maltotrioside from example 3a) is dissolved in 10 ml methanol and 25 ml tetrahydrofuran and 30 mg Pd on active charcoal (10% Pd, Merck 807104) are added.

It is hydrogenated for 2 hours while stirring vigorously without overpressure. The entire mixture is filtered from the catalyst, evaporated and after 30 minutes dried with a high vacuum pump.

Yield: 140 mg

TLC: $R_f$ 0.44 (silica gel, Merck 5735). mobile solvent 1-butanol/glacial acetic acid/water=10/3/5)

c) Isopropylidene-2',2,6-trichloro-indophenyl-α-D-maltotrioside 140 mg (0.2 mmol) isopropylidene-2-chloro-4-aminophenyl-α-D-maltotrioside from example 3b) is dissolved in 1.5 ml distilled, anhydrous dimethylformamide. 3 ml anhydrous dioxan and 3 drops BF$_3$-ethyl ether complex are added to this. It is cooled to 10° C. and 0.22 g (1.2 mmol) 2,6-dichlorobenzoquinone is added. It is stirred for 15 minutes at 10° C., then allowed to heat up to room temperature and stirred for a further 60 minutes.

40 ml diethyl ether is added to the reaction mixture whereupon the product flocculates. It is filtered and the residue is washed with diethyl ether. The product is obtained by purification on Sephadex LH20 (Pharmacia) using water as the eluent.

TLC: $R_f$=0.60 (silica gel, Merck 5735, mobile solvent 1-butanol/glacial acetic acid/water=10/3/5).

EXAMPLE 4

Synthesis of 2'-chloro-2-methyl-indophenyl-α-maltotrioside 3.5 g of the product from 1c) is dissolved in 15 ml anhydrous dimethylformamide, 60 ml anhydrous dioxan, 1.3 ml BF$_3$-ethyl ether complex and 2.45 g (20 mmol) 2-methyl-4-benzoquinone and 1 spatula-full of molecular sieve are added. The mixture is stirred overnight (16 h) at room temperature while excluding moisture. Subsequently 200 ml ethyl acetate is added and the precipitate which formed from this is aspirated over a G4 frit. The residue is dissolved in water and purified over a Sephadex LH 20 column.

Yield: 230 mg

TLC: $R_f$=0.44 (silica gel;

1-butanol/glacial acetic acid/water 10/3/5)

EXAMPLE 5

Synthesis of 2'-chloro-2,6-dimethyl-indophenyl-α-maltotrioside 500 mg of the product from 1c) is dissolved in 5 ml anhydrous dimethylformamide, 10 ml anhydrous dioxan, 0.2 ml BF$_3$-ethyl ether complex and 0.55 g (3 mmol) 2,6-dimethyl-4-benzoquinone and 2 spatula-fulls of molecular sieve are added. The mixture is stirred overnight at room temperature while excluding moisture. Subsequently 20 ml ethyl acetate and 20 ml diethyl ether are added and the precipitate which formed is aspirated over a G4 frit. This orange-red residue is dissolved in water and purified over a Sephadex LH 20 column.

Yield: 35 mg

TLC: $R_f$=0.44 (silica gel; 1-butanol/glacial acetic acid/water 10/3/5)

EXAMPLE 6

Use of substances produced according to example 4 and example 5 as substrates for the direct determination of α-amylase.

The procedure is analogous to example 2.

The results are shown in Table 2.

TABLE 2

| Substrate | Measurement wavelength [nm] | 400 mmol/l KSCN HPA relative value [ΔA/min] |
|---|---|---|
| 2',2,6-trichloro-indo-phenyl-α-maltotrioside (example 1) | 645 | 1 |
| 2'-chloro-2-methylindo-phenyl-α-maltotrioside (example 4) | 595 | 0.35* |
| 2'-chloro-2,6-dimethyl-indophenyl-α-malto-trioside (example 5) | 573 | 0.27* |

*measured at pH 8.0

We claim:

1. A compound of the formula (I):

in which Gluc is a glucose molecule and the indophenyl residue is linked to a (Glue) moiety by an α bond, wherein n is 1 or 2;

$R^1$ is a straight-chained or branched alkyl or alkoyl group with 1 to 6 carbon atoms, a cycloalkyl or cycloalkoyl group with 3 to 6 carbon atoms, a benzyl group, a benzyl group or a phenyl group; $R^2$ is H;

$R^3$, $R^4$, $R^5$, $R^6$, independently of one another represent hydrogen, a halogen, a nitro group, an acetamide group, a cyano group, a sulfonic acid group, a sulfinic acid group, a carboxylic acid group, a sulfonic acid alkyl ester group, a sulfinic acid alkyl ester group, a carboxylic acid alkyl ester group, a sulfonic acid amide group, a sulfinic acid amide group, a carboxylic acid amide group, an alkoxy group, a substituted or unsubstituted straight-chained or branched alkyl group with 1 to 6 carbon atoms, a substituted or unsubstituted cycloalkyl group with 3 to 6 carbon atoms, or a substituted or unsubstituted aryl group; or at least one of (i) $R^3$ and $R^4$ and (ii) $R^5$ and $R^6$ is linked to one another to form a condensed ring;

X and Y, independently of one another, represent hydrogen, a halogen, a nitro-group, an acetamide group, a cyano group, a sulfonic acid group, a sulfinic acid group, a carboxylic acid group, a sulfonic acid alkyl ester group, a sulfinic acid alkyl ester group, a carboxylic acid alkyl ester group, a sulfonic acid amide group, a sulfinic acid amide group, a carboxylic acid amide group, an alkoxy group, a substituted or unsubstituted straight-chained or branched alkyl group with 1 to 6 carbon atoms, a substituted or unsubstituted cycloalkyl group with 3 to 6 carbon atoms, or a substituted or unsubstituted aryl group;

provided that X and Y are not both hydrogens.

2. Compound of claim 1, wherein n is 2.

3. Compound of claim 1, wherein one of X or Y is hydrogen.

4. Compound of claim 1, wherein at least one of the residues X or Y is a halogen.

5. Compound of claim 4, wherein the halogen is chlorine.

6. Compound of claim 1, wherein $R^3$ and $R^5$ are both hydrogen and $R^4$ and $R^6$ are both halogens.

7. Compound of claim 6, wherein $R^4$ and $R^6$ are both chlorine.

8. 2',2,6-trichloro-indophenyl-α-maltotrioside.

9. Process for the preparation of a compound (I):

in which Gluc is a glucose molecule and the indophenyl residue is linked to a (Glue) moiety by an α bond, wherein n is 1 or 2;

$R^1$ is a straight-chained or branched alkyl or alkoyl group with 1 to 6 carbon atoms, a cycloalkyl or cycloalkoyl group with 3 to 6 carbon atoms, a benzoyl group, a benzyl group or a phenyl group; $R^2$ is H;

$R^3$, $R^4$, $R^5$, $R^6$, independently of one another represent hydrogen a halogen, a nitro group, an acetamide group, a cyano group, a sulfonic acid group, a sulfinic acid group, a carboxylic acid group, a sulfonic acid alkyl ester group, a sulfinic acid alkyl ester group, a carboxylic acid alkyl ester group, a sulfonic acid amide group, a sulfinic acid amide group, a carboxylic acid amide group, an alkoxy group, a substituted or unsubstituted straight-chained or branched alkyl group with 1 to 6 carbon atoms, a substituted or unsubstituted cycloalkyl group with 3 to 6 carbon atoms, or a substituted or unsubstituted aryl group; or at least one of (i) $R^3$ and $R^4$ and (ii) $R^5$ and $R^6$ is linked to one another to form a condensed ring;

X and Y, independently of one another, represent hydrogen, a halogen, a nitro group, an acetamide group, a cyano group, a sulfonic acid group, a sulfinic acid group, a carboxylic acid group, a sulfonic acid alkyl ester group, a sulfinic acid alkyl ester group, a carboxylic acid alkyl ester group, a sulfonic acid amide group, a sulfinic acid amide group, a carboxylic acid amide group, an alkoxy group, a substituted or unsubstituted straight-chained or branched alkyl group with 1 to 6 carbon atoms, a substituted or unsubstituted cycloalkyl group with 3 to 6 carbon atoms, or a substituted or unsubstituted aryl group;

provided that X and Y are not both hydrogens comprising the steps of (a) peracetylating maltose or maltotriose forming a compound of formula II:

in which Ac-GluC is a peracetylated glucose, Ac is an acetyl residue, O-Ac is an acetylated oxygen, and the acetyl residue at the reducing end of compound II is linked by a β bond to an Ac-Gluc moiety and (b) reacting the compound II, in the presence of an acid catalyst, with a substituted p-nitrophenol of the formula III to form a compound having formula IV, in which the p-nitrophenyl residue is linked to an Ac-Gluc moiety by an α bond,

(c) reducing the nitro group of compound IV to form a amino group, (d) cleaving the acetyl residues of the compound resulting from step c, (e) reacting the compound resulting from step d with a substituted or unsubstituted p-benzoquinone, having the formula V, to form a compound having the formula VI, in which the indophenyl residue is linked to an Ac-Gluc moiety by an α bond.

10. Process of claim 9, further comprising substituting positions 4 and 6 at the non-reducing end of the maltose or maltotriose residue by the residues $R^1$ and $R^2$, whereby a compound having the formula I is formed, 11. Method for determining the activity of α-amylase in an aqueous solution comprising contacting said aqueous solution with a compound of formula:

in which Gluc is a glucose molecule and the indophenyl residue is linked to a (Gluc) moiety by an α bond, wherein n is 1 or 2;
R¹ is hydrogen, a straight-chained or branched alkyl or alkoyl group with 1 to 6 carbon atoms, a cycloalkyl or cycloalkoyl group with 3 to 6 carbon atoms, a benzoyl group, a benzyl group or a phenyl group; R₂ is H;
R³, R⁴, R⁵, R⁶, independently of one another represent hydrogen, a halogen, a nitro group, an acetamide group, a cyano group, a sulfonic acid group, a sulfinic acid group, a carboxylic acid group, a sulfonic acid alkyl ester group, a sulfinic acid alkyl ester group, a carboxylic acid alkyl ester group, a sulfonic acid amide group, a sulfinic acid amide group, a carboxylic acid amide group, an alkoxy group, a substituted or unsubstituted straight-chained or branched alkyl group with 1 to 6 carbon atoms, a substituted or unsubstituted cycloalkyl group with 3 to 6 carbon atoms, or a substituted or unsubstituted aryl group; or
at least one of (i) R³ and R⁴ and (ii) R⁵ and R⁶ is linked to one another to form a condensed ring;
X and Y, independently of one another, represent hydrogen, a halogen, a nitro group, an acetamide group, a cyano group, a sulfonic acid group, a sulfinic acid group, a carboxylic acid group, a sulfonic acid alkyl ester group, a sulfinic acid alkyl ester group, a carboxylic acid alkyl ester group, a sulfonic acid amide group, a sulfinic acid amide group, a carboxylic acid amide group, an alkoxy group, a substituted or unsubstituted straight-chained or branched alkyl group with 1 to 6 carbon atoms, a substituted or unsubstituted cycloalkyl group with 3 to 6 carbon atoms, or a substituted or unsubstituted aryl group;
provided that X and Y are not both hydrogens,
to form a cleavage product and measuring said cleavage product as a determination of α-amylase, wherein said cleavage product is determined in the absence of an auxiliary enzyme.

12. Method of claim 11, wherein R¹ and R² are hydrogen.
13. Method of claim 11, wherein one of X or Y is hydrogen.
14. Method of claim 13, wherein the compound is 2',2,6-trichloro-indophenyl-α-maltotrioside.
15. Method of claim 11, wherein said α-amylase is pancreatic amylase, said method further comprising adding an inhibitor system for salivary α-amylase to said aqueous solution.

16. Method of claim 15, wherein said inhibitor system comprises at least one monoclonal antibody.
17. Reagent of claim 15, further comprising an inhibitor system for salivary α-amylase.
18. Reagent of claim 17, wherein the inhibitor system comprises at least one monoclonal antibody.
19. Reagent for the determination of α-amylase, comprising;
I. A compound of the formula (I):

in which Gluc is a glucose molecule and the indophenyl residue is linked to a Gluc moiety by an α bond, wherein n is 1 or 2;
R¹ is hydrogen;
R² is hydrogen
one of X or Y is hydrogen;
wherein when X is H, Y is a halogen, and when Y is H, X is a halogen;
R³, R⁴, R⁵, R⁶, independently of one another represent hydrogen, a halogen, a nitro group, an acetamide group, a cyano group, a sulfonic acid group, a sulfinic acid group, a carboxylic acid group, a sulfonic acid alkyl ester group, a sulfinic acid alkyl ester group, a carboxylic acid alkyl ester group, a sulfonic acid amide group, a sulfinic acid amide group, a carboxylic acid amide group, an alkoxy group, a substituted or unsubstituted straight-chained or branched alkyl group with 1 to 6 carbon atoms, a substituted or unsubstituted cycloalkyl group with 3 to 6 carbon atoms, or a substituted or unsubstituted aryl group; or
at least one of (i) R³ and R⁴ and (ii) R⁵ and R⁶ is linked to one another to form a condensed ring; and
II. an activator for α-amylase, wherein said activator is a thiocyanate salt.

20. Compound of the formula:

wherein Gluc is a glucose moiety and the indophenol residue is linked to said Gluc moiety by an α bond, wherein n is 1 or 2;
R¹ is hydrogen, a straight-chained or branched allyl or alkoyl group with 1 to 6 carbon atoms, a cycloalkyl or cycloalkoyl group with 3 to 6 carbon atoms, a benzoyl group, a benzyl group or a phenol group.
R² is hydrogen,
R³, R⁴, R⁵, and R⁶, independently of each other represent hydrogen, a halogen, a nitro group, an acetamide group, a cyano group, a sulfonic acid group, a sulfinic acid group, a carboxylic acid group, a sulfonic acid alkyl ester group, a sulfinic acid alkyl ester group, a carboxylic acid alkyl ester group, a sulfonic acid amide group, a sulfinic acid amide group, a carboxylic acid amide group, an alkoxy group, a substituted or unsubstituted straight-chained or branched alkyl group with 1 to 6 carbon atoms, a substituted or unsubstituted cycloalkyl group with 3 to 6 carbon atoms, or a substituted or unsubstituted aryl group; or at least one of (i) $R^3$ and $R^4$ and (ii) $R^5$ and $R^6$ is linked to one another to form a condensed rings ring, and X and Y, independently of each other, are an acetamide group, a carboxylic acid group, a sulfinic acid alkyl ester group, a carboxylic acid alkyl ester group, a sulfonic acid amide group, a carboxylic acid amide group, or a substituted or unsubstituted cycloalkyl group with 3 to 6 carbon atoms.

21. Process for the preparation of a compound (I):

in which Gluc is a glucose molecule and the indophenol residue is linked to a Gluc moiety by an α bond, wherein n is 1 or 2;

$R^1$ is hydrogen, a straight-chained or branched alkyl or alkoyl group with 1 to 6 carbon atoms, a cycloalkyl or cycloalkoyl group with 3 to 6 carbon atoms, a benzoyl group, a benzyl group or a phenol group;

$R^2$ is H;

$R^3$, $R^4$, $R^5$, $R^6$, independently of one another represent hydrogen, a halogen, a nitro group, an acetamide group, a cyano group, a sulfonic acid group, a sulfinic acid group, a carboxylic acid group, a sulfonic acid alkyl ester group, a sulfinic acid alkyl ester group, a carboxylic acid alkyl ester group, a sulfonic acid amide group, a sulfinic acid amide group, a carboxylic acid amide group, an alkoxy group, a substituted or unsubstituted straight-chained or branched alkyl group with 1 to 6 carbon atoms, a substituted or unsubstituted cycloalkyl group with 3 to 6 carbon atoms, or a substituted or unsubstituted aryl group; or at least one of (i) $R^3$ and $R^4$ and (ii) $R^5$ and $R^6$ is linked to one another to form a condensed ring; and X and Y, independently of one another, are an acetamide group, a carboxylic acid group, a sulfinic acid alkyl ester group, a carboxylic acid alkyl ester group, a sulfonic acid amide group, a carboxylic acid amide group, a substituted or unsubstituted cycloalkyl group with 3 to 6 carbon atoms, wherein the process comprises the steps of (a) peracetylating maltose or maltotriose forming a compound of formula II:

in which Ac-Gluc is a peracetylated glucose, Ac is an acetyl residue, O-Ac is an acetylated oxygen, and the acetyl residue at the reducing end of compound II is linked by a β bond to an Ac-gluc moiety and (b) reacting the compound II, in the presence of an acid catalyst, with a substituted p-nitrophenol of the formula III to form a compound having formula IV, in which the p-nitrophenol residue is linked to an Ac-Gluc moiety by an α bond,

(c) reducing the nitro group of compound IV to form an amino group, (d) cleaving the acetyl residues of the compound resulting from step c, (e) reacting the compound resulting from step d with a substituted or unsubstituted p-benzoquinone, having the formula V, to form a compound having the formula VI, in which the indophenol residue is linked to an Ac-Gluc moiety by an α bond.

* * * * *